(12) United States Patent
Tallarida et al.

(10) Patent No.: US 7,713,251 B2
(45) Date of Patent: *May 11, 2010

(54) IMPLANTABLE VASCULAR ACCESS DEVICE WITH CERAMIC NEEDLE GUARD INSERT

(75) Inventors: Steven J. Tallarida, Mansfield, MA (US); Mark Ettlinger, Lexington, MA (US)

(73) Assignee: STD Med, Inc., Stoughton, MA (US)

( * ) Notice: Subject to any disclaimer, the term of this patent is extended or adjusted under 35 U.S.C. 154(b) by 801 days.

This patent is subject to a terminal disclaimer.

(21) Appl. No.: 10/374,000

(22) Filed: Feb. 25, 2003

(65) Prior Publication Data

US 2003/0181878 A1 Sep. 25, 2003

Related U.S. Application Data

(63) Continuation of application No. 09/582,406, filed as application No. PCT/US99/28695 on Dec. 3, 1999, now Pat. No. 6,527,754.

(60) Provisional application No. 60/111,257, filed on Dec. 7, 1998.

(51) Int. Cl.
*A61M 31/00* (2006.01)
(52) U.S. Cl. .................................................. 604/288.04
(58) Field of Classification Search .............. 604/93.01, 604/288.01–288.04, 890.1, 891.1
See application file for complete search history.

(56) References Cited

U.S. PATENT DOCUMENTS

| | | | | |
|---|---|---|---|---|
| 4,190,040 A | * | 2/1980 | Schulte .................. 128/899 |
| 4,445,896 A | | 5/1984 | Gianturco .................. 604/238 |
| 4,543,088 A | * | 9/1985 | Bootman et al. ........ 604/288.02 |
| 4,576,595 A | | 3/1986 | Aas et al. .................... 604/256 |
| 4,673,394 A | | 6/1987 | Fenton, Jr. et al. .......... 604/175 |
| 4,781,680 A | * | 11/1988 | Redmond et al. ...... 604/288.02 |
| 4,802,885 A | | 2/1989 | Weeks et al. ................ 604/93 |
| 4,840,615 A | * | 6/1989 | Hancock et al. ........ 604/288.02 |
| 4,929,236 A | * | 5/1990 | Sampson .................... 604/175 |

(Continued)

FOREIGN PATENT DOCUMENTS

WO WO 97/01370 1/1997

OTHER PUBLICATIONS

Communication dated Jul. 30, 2003 received in EPO application No. 99 964 086.5 with Examiner's comments (5 pgs).

(Continued)

*Primary Examiner*—Nicholas D Lucchesi
*Assistant Examiner*—Christopher D Koharski
(74) *Attorney, Agent, or Firm*—Grossman Tucker Perreault & Pfleger PLLC

(57) ABSTRACT

The present invention provides an improved vascular access port comprising a port base with a metallic dish insert molded (or bonded) into the bottom of the reservoir. In one embodiment, a single reservoir is provided. In another embodiment, plural reservoirs are provided. The metallic bottom of the reservoir provides a hard surface that will resist abrasion and puncture by the access needles used to infuse medication or withdraw blood. Additionally, the single and dual ports can include exit ports that are intended to better anatomically fit into the subcutaneous areas around muscle tissue.

18 Claims, 4 Drawing Sheets

U.S. PATENT DOCUMENTS

| | | | |
|---|---|---|---|
| 5,041,098 A | 8/1991 | Loiterman et al. | 604/175 |
| 5,084,015 A * | 1/1992 | Moriuchi | 604/288.02 |
| 5,213,574 A | 5/1993 | Tucker | 604/93 |
| 5,295,658 A | 3/1994 | Atkinson et al. | 251/149.1 |
| 5,318,545 A | 6/1994 | Tucker | 604/244 |
| 5,332,398 A * | 7/1994 | Miller et al. | 604/175 |
| 5,338,398 A * | 8/1994 | Szwejkowski et al. | 438/720 |
| 5,360,407 A | 11/1994 | Leonard | 604/175 |
| 5,387,192 A | 2/1995 | Glantz et al. | 604/93 |
| 5,647,855 A * | 7/1997 | Trooskin | 604/175 |
| 5,718,682 A * | 2/1998 | Tucker | 604/244 |
| 5,792,104 A | 8/1998 | Speckman et al. | 604/93 |
| 5,833,654 A | 11/1998 | Powers et al. | 604/93 |
| 5,843,069 A | 12/1998 | Butler et al. | 604/891.1 |

OTHER PUBLICATIONS

Communication dated Mar. 9, 2004 received in EPO application No. 99 964 086.5 with Examiner's comments (4 pgs).

Communication dated December 15, 2005, received in EPO application No. 99 964 086.5 (9 pgs).

* cited by examiner

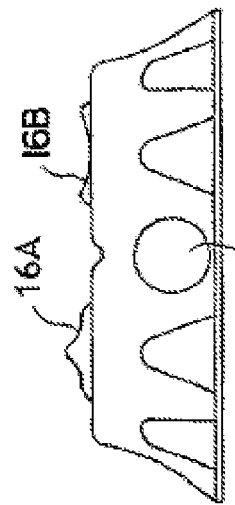
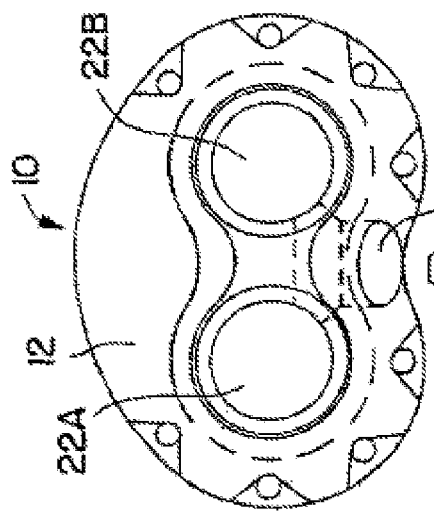
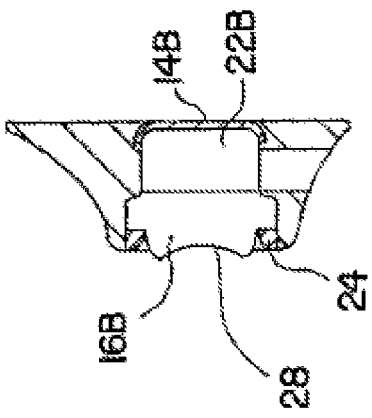
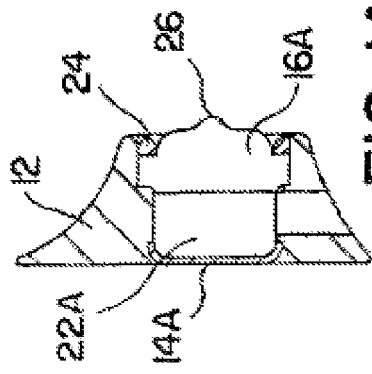

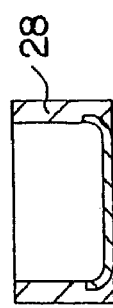
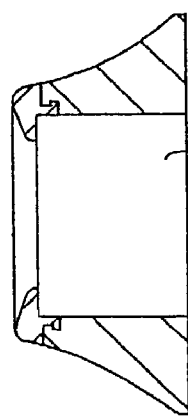
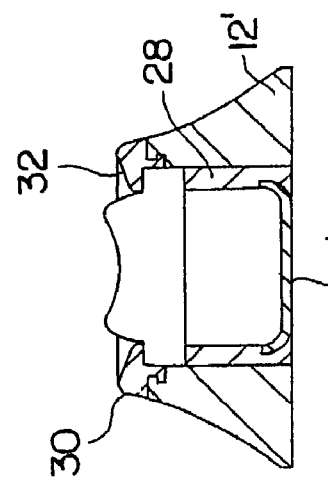

IMPLANTABLE VASCULAR ACCESS DEVICE WITH CERAMIC NEEDLE GUARD INSERT

This application is a continuation application of application Ser. No. 09/582,406, filed Jun. 23, 2000, now U.S. Pat. No. 6,527,754, which claims priority from PCT Application Serial No. PCT/US99/28695, filed Dec. 3, 1999, which claims priority from U.S. Provisional Application Ser. No. 60/111,257, filed Dec. 7, 1998, all of which are incorporated herein by reference.

BACKGROUND OF THE INVENTION

1. Field of the Invention

The present invention relates generally to a subcutaneously implantable vascular access port. More specifically, the present invention relates to an access port having a single needle-penetrable, self-sealing septum which affords repeated access to a plurality of distinct fluid cavities having staggered outlet ducts in communication with a plural lumen catheter.

2. Description of Related Art

Access portals, or ports, provide a convenient method to repeatedly deliver medicants to remote areas of the body without utilizing surgical procedures. The port is totally implantable within the body, and permits the infusion of medications, parenteral solutions, blood products, and other fluids. The port may also be used for blood sampling.

Known ports typically include a chamber accessible through a self-sealing septum. Septums of the prior art vary in shape, from a wafer-like cylindrical block of silicone to a pre-molded septum of U.S. Pat. No. 4,802,885 to Weeks et al. The pre-molded septum of U.S. Pat. No. 4,802,885 includes opposed convex surfaces and a peripheral ledge.

In common practice, a caregiver locates the septum of the port by palpitation. Port access is accomplished by percutaneously inserting a needle, typically a non-coring needle, perpendicularly through the septum of the port and into the chamber. The drug or fluid is then administered by bolus injection or continuous infusion. Ordinarily the fluid flows through the chamber, into a catheter and finally to the site where the fluid is desired. Except for the septum, traditional ports are constructed from all-metal or all-plastic. Each type of construction has unique advantages and disadvantages.

All-metal constructions have the advantages that they maintain a septum in a self-sealing fashion after repeated percutaneous injections. Additionally, all-metal constructions, such as titanium, or stainless steel provide a port which is both biocompatible and compatible with the injected fluid.

However, all-metal constructions present the disadvantages that they are relatively heavy, difficult to fabricate and relatively expensive. Additionally, all-metal ports produce large Magnetic Resonance Imaging (MRI) artifacts. On the other hand, all-plastic ports have the advantages that they are inexpensive to construct, light in weight, and do not create an MRI artifact. However, ports constructed from plastic have the disadvantage that infused fluids may react with the plastic body of the port. All-plastic ports contain the disadvantage that they cannot maintain a sealing engagement with the septum after repeated percutaneous injections. Additionally, all-plastic ports are susceptible to nicks and scratches on the interior surface by the accessing needle. These nicks and scratches could lead to nidus, blood clots, or precipitation formations.

Efforts have been made to combine the advantages of all-metal ports with all-plastic ports. For example, in U.S. Pat. No. 4,802,885 to Weeks et al., a metal reservoir having a chamber sealed by a pre-formed silicone septum is jacketed by a single piece of a silicone elastomer. However, all-metal ports jacketed by a single piece of elastomer have significant shortcomings. These shortcomings include quality control problems during manufacturing, and expensive molding processes.

Other efforts have focused on providing a multiple piece all-plastic housing in cooperation with an open metal cup to sealingly engage a septum. For example, see U.S. Pat. No. 5,213,574 to Tucker. This design has shortcomings associated with it, including defects in the plastic housing which may cause an improperly sealed septum. Once the septum is improperly sealed the entire port must be discarded.

Therefore a need has arisen for an access port device which addresses the problems of prior port devices.

A variety of implantable devices, known as subcutaneous access ports, are utilized to deliver fluids to or to withdraw fluids from the bloodstream of a patient. Such access ports typically include a needle-impenetrable housing which encloses one or more fluid cavities and defines for each such fluid cavity an access aperture communicating through the housing on the side thereof which is adjacent to the skin of the patient when the access port is implanted in the body. A needle-penetrable septum is received in and seals each access aperture. Exit passageways located in an outlet stem communicate with each of the fluid cavities for dispensing medication therefrom to a predetermined location in the body of the patient through an implanted catheter attached to the access port.

Once the access port and the catheter have been implanted beneath the skin of a patient, quantities of medication or blood may be dispensed from one such fluid cavity by means of a non-coring needle passed through the skin of the patient and penetrating the septum into one of the respective fluid cavities. This medication is directed through the distal end of the catheter to an entry point into the venous system of the body of the patient.

Blood may also be withdrawn for sampling from the body of a patient through such an access port. This is accomplished by piercing the skin of the patient and one of the respective septums with a non-coring needle and applying negative pressure thereto. This causes blood to be drawn through the catheter into the fluid cavity corresponding to the pierced septum and then out of the body of the patient through the needle.

To prevent clotting thereafter, the withdrawal route is flushed with a saline solution or heparin using again a non-coring needle piercing the skin of the patient and the septum in the same manner as if a medication were being infused.

Both intermittent and continual injections of medication may be dispensed by the access port. Continual access involves the use of a non-coring needle attached to an ambulatory-type pump or a gravity feed IV bag suspended above the patient. The ambulatory-type pump or the IV bag continually feeds the medication or fluid through the needle to the fluid cavity in the access port and from there through the catheter to the entry point into the venous system.

To facilitate locating each respective septum once the access port has been implanted, some access ports incorporate a raised circular ring located about the outer perimeter of the septum. This raised ring enhances the tactile sensation afforded by the subcutaneous septum to the palpating fingertip of a medical practitioner. Alternatively, other access ports have utilized palpation ridges rather than a raised circular ring for substantially the same purpose. The palpation ridges allow the location of the septum to be accurately determined when the access port is subcutaneously implanted.

To preclude reaction with the tissues in the body of the patient, access ports are constructed of nonreactive materials, such as titanium or stainless steel. Although these materials are nonreactive, access ports constructed utilizing titanium or stainless steel materials produce an interfering or blurred image of the body of the patient in the vicinity of the implanted access port when diagnostic imaging techniques such as magnetic resonance imaging ("MRI"), CAT scans, or computerized tomography are used. The blurred region caused by the presence of a metallic access port in the body of a patient extends beyond the access port itself. Therefore, the use of metallic access ports limits the diagnostic imaging techniques that may be used relative to those areas of the body in which an access port is implanted. In place of metallic materials some access ports have been fabricated at least in part from biocompatible plastics.

A further problem relating to the materials for and manufacture of access ports is the deleterious impact of some manufacturing procedures on the fluids which flow through the fluid cavities and related structures located between the fluid cavities and the catheter. During the manufacture of an access port, whether the port is comprised of metallic or plastic materials, it becomes necessary to form the fluid cavities and exit passageways through which the fluid will be directed into the attached catheter. This manufacturing process often leaves sharp edges, seams and corners in the areas where the fluid cavity is to direct the flow of the fluid through an exit passageway. As blood or other fluids are injected through the septum into the fluid cavity, pressure developed within the fluid cavity tends to cause fluid to flow through the exit passageway. As the fluid in the fluid cavity flows past the sharp edges and corners produced in the manufacture of the access port, turbulence arises, taking the form of a vortex, adjacent to the sharp edges and corners. Some fluids, such as blood, are sensitive to this turbulence, and lysing of the red blood cell component of the injected blood can occur in these turbulent areas.

In addition, the production of the circular fluid cavities often results in the creation of areas within the housing in which fluid flow is retarded. These areas are referred to as dead spaces and usually occur in areas of transition, such as where the bottom of the septum interfaces with the walls of the fluid cavity and where the floor of the fluid cavity meets the exit passageway through which the fluid must flow. As the flow of fluids through dead spaces is retarded, stagnation occurs, resulting in some fluid being trapped within these dead spaces. If the access port is used to withdraw or transfuse blood, blood trapped in these dead spaces may form clots and block the flow of fluid through the fluid cavity.

Moreover, in some prior vascular access ports the internal reservoirs are formed by two plastic parts with are bonded together. This results in an undesirable seam being formed where the adjacent parts abut one another. The inside of the reservoir should be as smooth as possible to help prevent damage to blood cells or the initiation of blood clotting during infusion or withdrawal of blood through the port.

A further problem encountered in the design and construction of access port relates to the positioning of the septums within the housing of the access port. The positioning of the septums within the housing is a compromise between two conflicting objectives. These are the need to separate the septums to such a distance so that the septums may be easily differentiated for the purpose of injection and the need to restrict the overall dimensions of the access port for patient comfort and aesthetics. The distancing of the septums to facilitate their differentiation, however, results in a corresponding distancing of the fluid cavities. This result is at odds with another structural requirement for access ports with plural cavities, namely that the exit passageways from each fluid cavity be closely spaced at the point where the implanted catheter is to be coupled to the access port.

To guide the flow of a fluid from each of the spatially separated fluid cavities into the side-by-side configuration of fluid outflow necessitated by the dimensions of a plural lumen catheter, intermediate structural members have been required. Naturally, this complicates the process of manufacture and increases its cost, as well as the changes of structural failure.

There are several examples of such intermediate members used to resolve the manufacturing constraints imposed upon the construction of a passageway flowing from spatially separate fluid cavities into a side-by-side configuration acceptable by a catheter. One is to produce passageways in the form of bent metal tubes which are then insert molded or welded into the larger body of the access port. The use of such a metal component will interfere with the production of an access port which is free of limits as to the diagnostic imaging techniques that may be used relative to those areas of the body in which an access port is implanted. In addition, the integral nature of such metal outlet passageways raises the possibility of leakage of medication through the interstices between the metal tubes and the body of the access port.

Alternatively, to produce fluid flow from spatially separated fluid cavities into the closely spaced lumens of a catheter, each fluid cavity has been designated with its own spatially separated outlet stem. These outlet stems are then coupled by a hub structure for permanent attachment to the closely spaced lumens of a catheter. This type of arrangement increases the size of the overall access port and its cost of manufacture by adding thereto the necessity of fabricating and assembling of the hub element. Port connections to catheters in this manner are permanent. Accordingly, if the catheter is to be shortened by trimming, that trimming must occur at the distal end of the catheter, and this precludes the use of any type of specially designed tip or valve.

An additional set of problems encountered in the use of access ports relates to the actual connection of the catheter to the access port. This is most commonly effected by securing the catheter to an outlet stem protruding from the housing of the access port. In an attempt to lock the catheter to the outlet stem of the access port, thread-type systems have been developed wherein the catheter is attached to an outlet stem, and the outlet stem is then threaded into the access port. When utilizing this system, however, it is difficult to determine the amount of engagement of the catheter onto the outlet stem. Some catheter connection systems do not allow visual verification of attachment. As a result, leakage and failure can occur.

To overcome this problem, access ports are produced in which the catheter is pre-attached at the factory. While this practice alleviates many of the problems with leakage and failure due to catheter slippage, this system severely limits the type of the catheter usable with the access port. This precludes the use of catheters having specialized distal tips, as the distal end of the catheter is the only end that can then be trimmed to effect its ultimate sizing. For example, catheters utilizing a Groshong.RTM. slit valve at their distal end may not have any of the distal tip of the catheter removed without compromising the catheter.

Thus, there has been a need for an improved vascular access port which overcomes the above-noted problems, and which can be manufactured economically. The present invention fulfills these needs and provides other related advantages.

SUMMARY OF THE INVENTION

Accordingly, the present invention provides an improved vascular access port comprising a plastic port base with a metallic dish insert molded (or bonded) into the bottom of the reservoir. In one embodiment, a single reservoir is provided. In another embodiment, plural reservoirs are provided. The metallic bottom of the reservoir provides a hard surface that will resist abrasion and puncture by the access needles used to infuse medication or withdraw blood. The features of both the single and dual ports include 'duck tail' rears. This feature is intended to better anatomically fit into the subcutaneous areas around muscle tissue. The plastic must be of a bio-compatible and chemically-compatible material such as Nylon, Poly Acetals, or Polyethersulphone. The chemical resistance is necessary so that the injected medications do not react with the port materials. The yield and creep strength and flexure modulus of the material is important so that the plastic will hold and retain the port top retaining the septum.

In the preferred embodiment, the present invention provides an implantable access port, comprising a housing member defining at least one fluid chamber. A cup member is attached to the housing member and defining the bottom of the fluid chamber. A permeable septum member is attached to the housing and defining the top of the fluid chamber and having a tactile or visual location marker portion on the outer surface thereof. An exit port is provided to permit egress of fluid from within the fluid chamber.

The cup may be made of stainless steel, titanium or ceramic (alumina or zirconium). All these materials are biologically and chemically inert so that they will not react with the body or medications. The insert is formed, cast, machined or molded into a 'dish' shape with the edges being of a radius greater than 0.035". This radius is important for the reduction of coagulation and turbulence of the blood and medication within the reservoir.

The port assembly can include a top or retaining ring(s). This top retains the rubber septum. It can be made of the same plastic material as the base; in which case, it can be fit, bonded or ultra-sonically welded to the base after septum placement. It can be a metallic material as mentioned above for the dish insert. For these applications the attachment of the top can be achieved by interference fits, bonding with a biocompatible epoxy or by various welding means (ultrasonic, friction, or thermal melt).

Each port has a stem or catheter adapter which enables a fluid path between the reservoir and the external catheter traveling to the vascular area. Stems are made from biocompatible and chemically inert materials that are also strong such as stainless steel or titanium. The stem for the single port has one fluid channel straight through its body. The dual version has two channels which angle out to the sides in order to meet with the walls of the reservoirs. Both these stems have barbs for locking into the plastic body. Barb(s) are also found on the distal end for attachment to the catheter. The dual version has a split between the channel holes in order to allow a bi-lumen catheter to attach.

The septums for these ports are intended to assist in the location (and in the case of the dual port) differentiation of the reservoir location. The combinations for these may vary for application preferences. The two styles include concave and convex shapes. After the surgical implantation, the location is determined by palpitation of the skin over the port. For the illustration shown, the concave side feels different than the convex side. The convex feature has a nipple shape. Both septums are designed to fit into the port body and be retained by the port top. The septum is intended to be self sealing under the pressures produced by the vascular system and the injection pressures of injections. This is achieved by controlling the rubber hardness and the dimensions relative to the retained assembly. The interference fit or squeezing of the septum rubber creates a residual pressure radially toward the center of the septum. The softness of the rubber allows the punctures to reseal without leakage. It is preferred that non-coring needles are used by clinical staff to avoid excessive reduction of material and coring or skiving material into the reservoir which flow into the blood stream. The rubber material commonly used for septums is silicone, but other biocompatible elastomer materials may be used.

Advantageously, the present invention provides low cost, yet durable subcutaneous vascular access port(s). The port(s) can be manufactured from bicompatible grades of plastics and metals which meets the safety and clinical parameters of implanted devices. This plastic port features a metallic (titanium, stainless steel or ceramic) dish which will be insert molded pressed, or bonded into the base of the port reservoir to prevent potential penetration of needles through the base of a typical style plastic port. Also advantageously, the port of the present invention features a titanium shield molded into a plastic port top around the rubber septum to prevent needle mislocation, false needle locations and potential medication misdirection. The port septums have incorporate in them indication features to distinguish which port reservoir the surgeon or nurse is accessing and better locates the reservoir center. These features are utilized in other dual lumen ports by an indication on the port itself, but not on the septum.

Other features and advantages of the present invention will become apparent as the following Detailed Description proceeds, and upon reference to the Drawings, wherein like numerals depict like parts, and wherein:

BRIEF DESCRIPTION OF THE DRAWINGS

FIGS. 1A-1D depict various views of the preferred dual-port implantable access device of the present invention;

FIG. 3A-3D depict various views of another embodiment of the implantable access device of the present invention;

DETAILED DESCRIPTION OF PREFERRED EMBODIMENTS

Figure 2C:
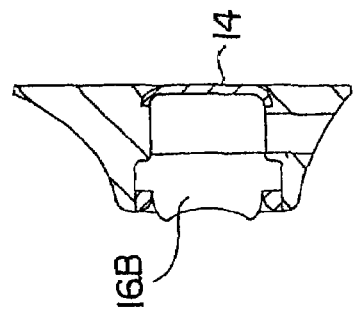
FIGS. 2A-2E depict various views of the preferred single-port implantable access device of the present invention.
Figure 2E:
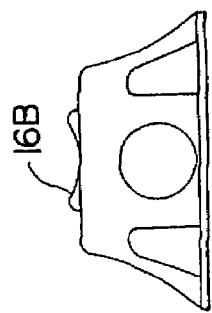
Figure 2B:
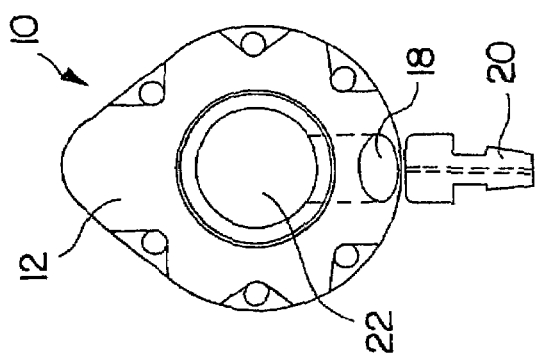
Figure 2D:
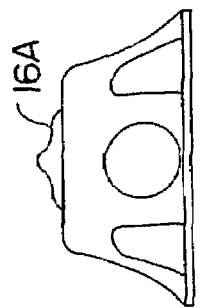
Figure 2A:
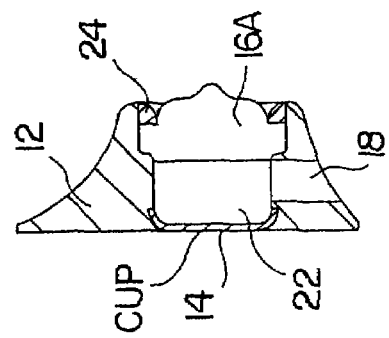

FIGS. 1A-1D depict various views of the preferred dual-port implantable access device 10 of the present invention. The port 10 generally comprises a housing member 12 defining fluid chambers 22A and 22B. The chambers are sealed by the housing 12, bottom cup members 14A and 14B, and self-sealing septum members 16A and 16B. In this embodiment, the housing 12 is preferably formed of titanium, stainless steel, ceramic, and/or other biocompatible material. The septum 16A and 16B is preferably formed of silicon or other semi-permeable materials that permit ingress and egress of needles to deliver fluid to the chambers 22A and/or 22B. An exit port 18 is provided in communication with chambers 22A and 22B, which delivers fluid out of the chambers 22A and/or 22B to a predetermined location, via stem 20 and attached catheter (not shown), as is understood in the art.

The septums 16A and 16B are formed with a generally circular shape, and, as shown in the drawings, may include a nipple 26 or a concave portion 28 on the outer surface thereof. The nipple is advantageous for visual and/or tactile location of the port device 10, and as a locator for needle insertion. Likewise, concave portion 28 provides similar features, but may be used in areas where a protruding nipple is undesirable. The septums 16A and 16B and housing 12 are preferably formed with mated tongue and groove portions, as shown in the side view drawings of FIGS. 1A and 1C. The housing may further include molded top member 24 which press against the septum for further stability.

As opposed to plastic materials used in the prior art, the bottom cup members 14A and 14B are preferably formed of titanium or stainless steel to resist scratches and/or debris from being introduced into the chambers, as a result of needle impacts thereon. Preferably, bottom cup members 14A and 14B are attached to housing 12 via insert molding, interference fit, ultrasonic weld, biocompatible glue, and/or other attachment means. FIGS. 2A-2E depict a single-port version of the port device of the present invention, and is similarly constructed as shown in FIG. 1A-1D.

FIG. 3A-3D depict another embodiment of the port device of the present invention. In this embodiment, the cup member 14' includes sidewall portions 28 that are dimensioned to fit within the chamber 22', defined by housing 12'. The cup member 14' is attached to the housing 12' by insert molding, interference fit, ultrasonic weld, biocompatible glue, or other attachment means known in the art. The septum 16' is similar to the septum 16A and/or 16B and may also include a nipple or concave portion, described above. In this embodiment, a metal ring 30 is provided which circumscribes the top of the housing 12' and is positioned above the septum 16'. The ring 30 preferably includes flange members 32, which have an upper surface dimensioned so as to urge a needle downward toward the septum, thus preventing errant entry of needles within the septum. In this embodiment the ring structure is formed of titanium, stainless steel or ceramic material for increase mechanical resistance to puncture and/or tear. Accordingly, since the ring member 30 will protect the other components, the housing can be formed of less expensive material, e.g., plastics, etc. The ring member 30 and housing 12' preferably include mated tongue and groove portions to hold the ring member securely against the housing, as shown. Additionally, the lower surface of the flange members 32 are dimensioned so as to force against the septum, thereby holding the septum in place.

Figure 4:
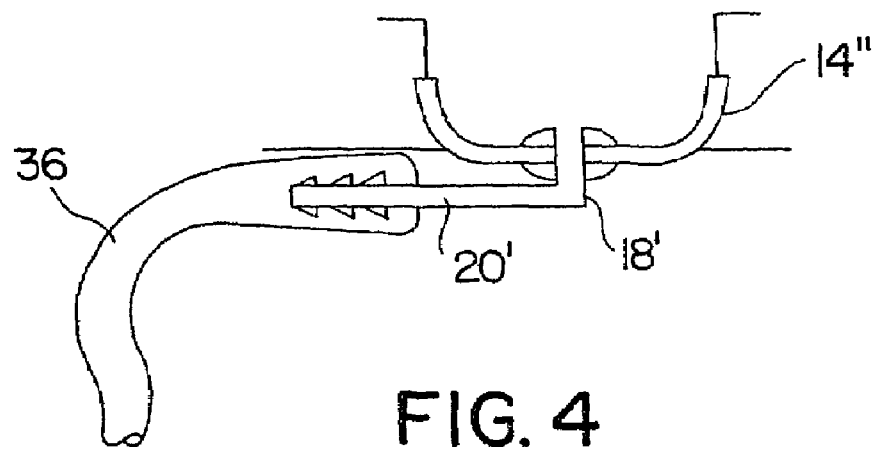
FIG. 4 depicts an alternative embodiment of the cup member of FIGS. 1-3.
Figure 5A:
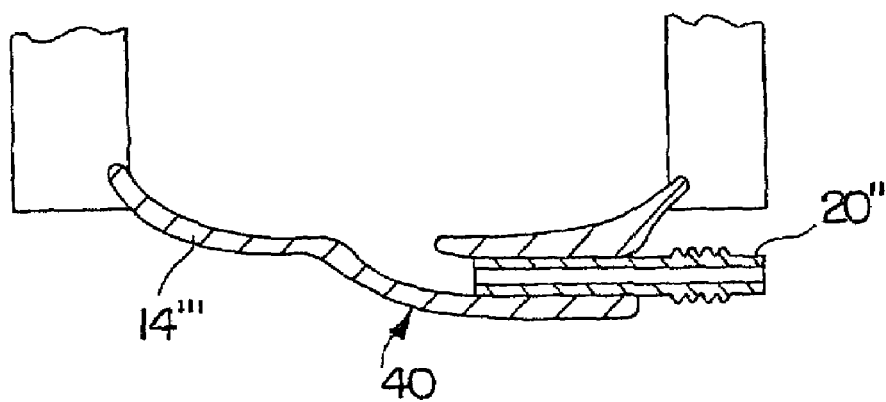
FIGS. 5A and 5B depict views of another alternative embodiment of the cup member of FIGS. 1-3.
Figure 5B:
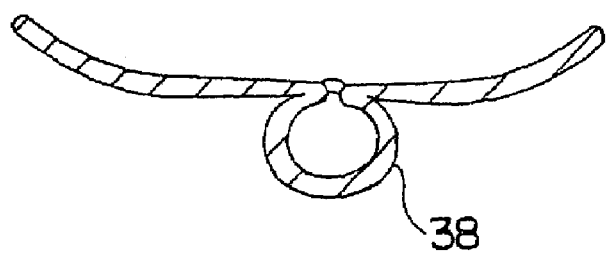

FIGS. 4 and 5A-5B depict alternative embodiments for the cup member described above in FIGS. 1-3. In the embodiment of FIG. 4, the cup member 14" defines an exit port 18' therein, and preferably located at the bottom portion of the cup 14", as shown. A stem 20' is connected to the port 18' at one end, and a catheter 36 is connected to the other end of the stem 20'. So as to provide a low-profile shape, it is preferred that the stem 20' includes an elbow, or angled portion, to direct fluid sideways away from the port, as shown. In FIGS. 5A and 5B, the cup 14'" is formed with a flange 40 to define an opening 38 that is dimensioned to accept a stem 20" therein. The cup 14" and/or 14'" are provided to better anatomically fit into the subcutaneous areas around muscle tissue, and each are connected to the housing (not shown) in a manner similar to the embodiments of FIG. 1, 2 or 3.

Thus, it is apparent that there has been provided an implantable vascular access device that satisfies the objectives set forth herein. Those skilled in the art will recognize that the present invention is subject to modification and/or alterations, all of which are deemed within the scope of the present invention, as defined in the appending claims.

What is claimed is:

1. An implantable access port, comprising
a plastic housing member comprising a first side wall portion of at least one fluid chamber and an exit port in the side wall in fluid communication with said fluid chamber,
a permeable septum member attached to said housing and defining a top of said fluid chamber, and
an insert member comprising a concaved-shape having a base portion covering a bottom of said fluid chamber, an edge radius extending generally outwardly from said base portion generally towards said permeable septum member, and a second side wall portion of said fluid chamber extending from said edge radius only to a point at or below said exit port of said fluid chamber, wherein said insert member comprises a material selected from the group consisting of stainless steel, titanium or ceramic, and wherein a volume of said at least one fluid chamber is defined by said permeable septum, said first side wall portion of said plastic housing member, said second side wall portion of said insert member and said base portion of said insert member.

2. A port as claimed in claim 1, said septum further comprising a tactile or visual location marker portion on the outer surface thereof.

3. A port as claimed in claim 1, wherein said septum is formed of silicone, and permits the ingress and egress of needles to deliver fluid to said fluid chamber.

4. A port as claimed in claim 1, wherein said housing is dimensioned so as to be placed within a predetermined position under skin.

5. A port as claimed in claim 1, wherein said tactile or visual location marker portion of said septum comprises a nipple on the outer surface thereof.

6. A port as claimed in claim 1, wherein said tactile or visual location marker portion of said septum comprises a concave portion on the outer surface thereof.

7. A port as claimed in claim 1, wherein said edge radius is greater than 0.035".

8. An implantable access port, comprising
a plastic housing member comprising a first side wall portion of at least one fluid chamber and an exit port in the side wall in fluid communication with said fluid chamber,
a permeable septum member defining a top of said fluid chamber;
at least one ring circumscribing a top of said housing member above said permeable septum, said at least one ring configured to be secured to said plastic housing member and comprising flange members having an upper surface which tapers inwardly towards said permeable septum such that at least one apex of said tapered flange members is disposed at or below said permeable septum, said flange members configured to urge a needle toward said permeable septum, said at least one ring further configured to secure said permeable septum to said port; and
an insert member comprising a concaved-shape having a base portion covering a bottom of said fluid chamber, an edge radius extending generally outwardly from said base portion generally towards said permeable septum member, and a second side wall portion of said fluid chamber extending from said edge radius only to a point at or below said exit port of said fluid chamber, wherein said insert member comprises a material selected from the group consisting of stainless steel, titanium or ceramic, and wherein a volume of said at least one fluid chamber is defined by said permeable septum, said first side wall portion of said plastic housing member, said second side wall portion of said insert member and said base portion of said insert member.

9. The port of claim 8, wherein said at least one ring and said housing comprise mated tongue and groove portion configured to secure said at least one ring to said housing.

10. The port of claim 9, wherein said at least one ring comprises a metal ring.

11. The port of claim 9, wherein said at least one ring comprises a material selected from the group consisting of titanium, stainless steel or ceramic material.

12. The port of claim 8, wherein a lower surface of said flange members is configured to secure said permeable septum to said port.

13. An implantable access port, comprising
a plastic housing member comprising a first side wall portion of at least one fluid chamber and an exit port in the side wall in fluid communication with said fluid chamber,
a permeable septum member attached to said plastic housing member and defining a top of said fluid chamber;
at least one ring circumscribing a top of said housing member above said permeable septum, said at least one ring configured to be secured to said plastic housing member and to comprising flange members having an upper surface which tapers inwardly towards said permeable septum such that at least one apex of said tapered flange members is disposed at or below said permeable septum, said flange members configured urge a needle toward said permeable septum, said at least one ring further configured to secure said permeable septum to said port and to include a material selected from the group consisting of metal or ceramic material; and
an insert member defining a bottom and a second side wall portion of said fluid chamber, wherein said insert member comprises a material selected from the group consisting of stainless steel, titanium or ceramic, and wherein a volume of said at least one fluid chamber is defined by said permeable septum, said first side wall portion of said plastic housing member, said second side wall portion of said insert member and said base portion of said insert member.

14. The port of claim 13, wherein said at least one ring and said housing comprise mated tongue and groove portion configured to secure said at least one ring to said housing.

15. The port of claim 13, wherein a lower surface of said flange members is configured to secure said permeable septum to said port.

16. The port of claim 13, wherein said at least one ring comprises a metal ring.

17. The port of claim 16, wherein said at least one ring comprises a material selected from the group consisting of titanium or stainless steel.

18. The port of claim 13, wherein said at least one ring comprises a ceramic ring.

* * * * *

UNITED STATES PATENT AND TRADEMARK OFFICE
CERTIFICATE OF CORRECTION

| | | |
|---|---|---|
| PATENT NO. | : 7,713,251 B2 | Page 1 of 1 |
| APPLICATION NO. | : 10/374000 | |
| DATED | : May 11, 2010 | |
| INVENTOR(S) | : Steven J. Tallarida et al. | |

It is certified that error appears in the above-identified patent and that said Letters Patent is hereby corrected as shown below:

Title Pg, Item (54), Title: delete "IMPLANTABLE VASCULAR ACCESS DEVICE WITH CERAMIC NEEDLE GUARD INSERT" and insert -- IMPLANTABLE VASCULAR ACCESS DEVICE --, therefor.

In column 1, line 1-2, delete "IMPLANTABLE VASCULAR ACCESS DEVICE WITH CERAMIC NEEDLE GUARD INSERT" and insert -- IMPLANTABLE VASCULAR ACCESS DEVICE --, therefor.

In column 1, line 3, below Title, insert -- CROSS REFERENCE TO RELATED APPLICATIONS --, as a heading.

Signed and Sealed this

Thirty-first Day of August, 2010

David J. Kappos
*Director of the United States Patent and Trademark Office*